(12) United States Patent
Hirai et al.

(10) Patent No.: US 8,587,644 B2
(45) Date of Patent: Nov. 19, 2013

(54) IMAGE PROCESSING APPARATUS FOR ENDOSCOPE

(75) Inventors: Tsutomu Hirai, Sagamihara (JP); Akihito Kawamura, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1139 days.

(21) Appl. No.: 11/916,721

(22) PCT Filed: Jun. 2, 2006

(86) PCT No.: PCT/JP2006/311110
§ 371 (c)(1),
(2), (4) Date: Dec. 6, 2007

(87) PCT Pub. No.: WO2006/132154
PCT Pub. Date: Dec. 14, 2006

(65) Prior Publication Data
US 2009/0027490 A1    Jan. 29, 2009

(30) Foreign Application Priority Data
Jun. 6, 2005  (JP) ................. 2005-166203

(51) Int. Cl.
*H04N 9/47*  (2006.01)
(52) U.S. Cl.
USPC .................. 348/65; 348/45; 348/46; 348/70; 348/71; 348/72; 348/73; 348/74; 348/75; 348/76; 348/77
(58) Field of Classification Search
USPC ................................ 348/45, 46, 65, 70–77
See application file for complete search history.

(56) References Cited

U.S. PATENT DOCUMENTS

2004/0085442 A1    5/2004  Kawata
2004/0101277 A1*   5/2004  Endo ............................. 386/46
(Continued)

FOREIGN PATENT DOCUMENTS

EP    1 779 766 A1    5/2007
JP    2000-341553    12/2000
(Continued)

OTHER PUBLICATIONS

Extended Supplementary European Search Report dated Oct. 4, 2010.
(Continued)

*Primary Examiner* — Liangche A Wang
*Assistant Examiner* — Cheikh Ndiaye
(74) *Attorney, Agent, or Firm* — Scully, Scott, Murphy & Presser, P.C.

(57) ABSTRACT

This is an endoscope apparatus which has an endoscope which picks up an image of a sample using a solid state image pickup element and outputs an image pickup signal, and a processor which processes the above-mentioned image pickup signal, generates HDTV and SDTV serial digital video signals, switches one side of those selectively, and performs a serial output, in which the serial digital video signal switched selectively by the above-mentioned processor is output through a first connector, the above-mentioned processor is equipped with a discrimination signal generating section which is linked with selection switching of the above-mentioned HDTV or SDTV serial digital video signal to generate an HDTV/SDTV discrimination signal which can discriminate the above-mentioned HDTV or SDTV serial digital video signal, and the discrimination signal is output through a second connector different from the above-mentioned first connector.

2 Claims, 8 Drawing Sheets

(56) References Cited

U.S. PATENT DOCUMENTS

2004/0196364 A1 10/2004 Takahashi
2005/0020879 A1 1/2005 Suzuki
2005/0231591 A1* 10/2005 Abe ............................. 348/65
2005/0253950 A1* 11/2005 Miura ..................... 348/333.11

FOREIGN PATENT DOCUMENTS

| JP | 2001-005902 | 1/2001 |
| JP | 2002-085342 | 3/2002 |
| JP | 2004-305373 | 11/2004 |
| JP | 2005-118074 | 5/2005 |
| JP | 2005-124823 | 5/2005 |
| JP | 2006-043207 | 2/2006 |
| WO | WO 2004/086748 A2 | 10/2004 |
| WO | WO 2006/013795 A1 | 2/2006 |

OTHER PUBLICATIONS

European Official Action dated Apr. 24, 2012 from related application EP 06 756 931.9-2319.

* cited by examiner

| VENDOR ID, 24 bits | SPECIFIC ID, 40 bits |
|---|---|
| 000000 (h) | AAAAAAAAAA (h) |

IMAGE PROCESSING APPARATUS FOR ENDOSCOPE

TECHNICAL FIELD

The present invention relates to an image processing apparatus for an endoscope which generates various kinds of video signals from an image pickup signal by a solid state image pickup element mounted in the endoscope.

BACKGROUND ART

In recent years, endoscope systems which perform endoscopy and endoscopic diagnosis by displaying endoscope images, picked up by an image pickup section using a solid state image pickup element, on a display unit have spread widely.

In addition, in an endoscope system, it is possible to perform monitor display with selecting a pickup image by an endoscope and a screen image of an external device, such as a video printer and an image filing apparatus.

On the other hand, a digital video signal has an advantage that there is less attenuation of signal strength at the time of transmission, degradation, and incorporation of less noise in comparison with an analog video signal, and hence, ones corresponding to a digital video signal have increased in video processors and peripheral devices (including monitors also) connectable to these.

In addition, as for endoscope image signals picked up with solid state image pickup elements, there are also endoscope systems which can output two kinds of video signals, an SDTV signal (standard image signal) and an HDTV signal (e.g., an high-definition video signal), from a video processor.

Furthermore, it is also performed to lessen a number of signal lines by multiplexing a luminance signal and color-difference signals into a serial signal when transmitting a digital video signal of an endoscope image to a monitor after performing signal processing of it, and further multiplexing machine type information of the endoscope, and a control signal, based on an instruction by an operation section, in a blanking period of the serial digital video signal (e.g., refer to Japanese Patent Laid-Open No. 2004-305373).

By the way, when making two kinds of video signals, an SDTV signal and an HDTV signal, taken in from an image pickup section into serial digital video signals by a video processor respectively, and switching them into one of the serial digital video signals according to an instruction by the operation section to output it to an external device, when outputting and storing it on storing devices such as a DVD while outputting and displaying it on a monitor such as a liquid crystal display device, display switching of the SDTV signal and the HDTV signal is performed in an instant without a temporal gap in a monitor by a selection switching signal on the basis of the instruction by the operation section, but, since storage switching in a storing device was performed by analyzing and discriminating the SDTV signal and the HDTV signal in a storing device side, it needed time to execute an analysis and discrimination algorithm, switching was not performed in an instant, and there might arise delay, for example, in switching to HDTV from SDTV.

For this reason, there was an issue of generating a little lack in a video of the HDTV signal to be stored next when switching, for example, from the SDTV signal to the HDTV signal. Since lasers at different wavelengths are used when storing the SDTV signal and the HDTV signal, the switching delay in the storing device side at the time of the storage arises also in laser switching with following the switching of the SDTV signal and the HDTV signal.

A method of generating the delay as less as possible according to the switching of the video processor which is a delivery side is necessary for switching control in a side of an external device, in particular a storing device.

Then, in view of the above-mentioned issue, an object of the present invention is to provide an image processing apparatus for an endoscope which performs switching of video storage of an SDTV signal and an HDTV signal in an instant in a storing device according to switching in a processor side hardly to generate a period when a stored video stops.

A second object is to provide an image processing apparatus for an endoscope in an endoscope system which can specify an endoscope apparatus from a filed digital video signal even if a malfunction arises in a switching (selection) section in the case of filing with selectively switching digital video signals from a plurality of endoscope apparatuses.

A third object is to provide an image processing apparatus for an endoscope which can perform effective or good (suitable) processing as an endoscope image by changing amplitude of a dynamic range between an output in an analog video signal, and an output in a digital video signal when outputting a video signal, on which digital processing is performed, to external devices such as a monitor, or changing amplitude of a dynamic range of a digital video signal according to an endoscope to be used.

DISCLOSURE OF INVENTION

Means for Solving the Problem

An image processing apparatus for an endoscope in a first aspect of the present invention is featured by including a video signal generating section which processes an image pickup picture signal from an endoscope which picks up an image of a sample using a solid state image pickup element to generate two or more kinds of serial digital video signals whose resolutions are different, a first connector which outputs a serial digital video signal selected on the basis of a selection instruction for selecting one of the two or more kinds of serial digital image pickup signals generated, a discrimination signal generating section which generates a discrimination signal which enables discrimination of the serial digital video signal, which is selected on the basis of the selection instruction, with being linked with selection switching of the two or more kinds of serial digital video signals, and a second connector which outputs the discrimination signal.

According to the aspect, with being linked with switching of two or more kinds of serial digital video signals whose resolutions in a processor side are different switching of video storage of two or more kinds of serial digital video signals whose resolutions in a storing device are different is performed more quickly. It is possible to further reduce a period when a stored video image stops. Thus, lack of stored video image is hardly generated and it is possible to reproduce faithfully a diagnostic video of an endoscope.

An image processing apparatus for an endoscope in a second aspect of the present invention is an image processing apparatus for an endoscope which processes an image pickup signal from an endoscope equipped with a solid state image pickup element to output a serial digital video signal, which is featured by having an additional information insertion section which inserts additional information set in a video blanking period of the serial digital video signal.

According to the aspect, when switching serial digital video signals from a plurality of endoscope apparatuses selectively and files it, it is possible to more reliably specify an endoscope apparatus and a patient, which are video sources, from additional information, such as a specific identification number and a patient ID, which are included in the filed serial digital video signal, even if a malfunction arises in a switching (selection) section.

An image processing apparatus for an endoscope in a third aspect of the present invention is featured by including a digital converting section which performs digital conversion of an image pickup signal from an endoscope equipped with a solid state image pickup element, and outputs a digital video signal, a dynamic range converting section which converts a dynamic range of the digital video signal output from the digital converting section and outputs it, and a D/A converting section which performs analogue conversion of the digital video signal output from the digital converting section without passing the dynamic range converting section.

According to the aspect, when outputting a digital video signal, which is given digital processing by a processor, to external devices such as a monitor, it is possible to perform effective processing which is suitable to a standard as an endoscope image by changing a dynamic range between an output in an analog video signal, and an output in a digital video signal. Amplitudes of dynamic ranges of a digital video signal and an analog video signal are different on the standard, amplitude of a dynamic range corresponding to either one of signals was used conventionally, and hence, an optimum video signal was not obtained for the other signal.

An endoscope apparatus according to the present invention is featured by including a digital converting section which receives an image pickup signal from an endoscope equipped with a solid state image pickup element, performs digital conversion of the image pickup signal, and outputs a digital video signal, a dynamic range converting section which receives the digital video signal converted by the digital converting section, converts a dynamic range of the digital video signal, and outputs it, and an information inputting section into which information regarding the endoscope which outputs the image pickup signal is input, and in that the dynamic range converting section is configured so as to change amplitude of a dynamic range of the digital video signal on the basis of information regarding the endoscope input into the information inputting section.

According to the aspect, when outputting a video signal, on which digital processing is performed, to external devices such as a monitor, it is possible to enhance image quality by performing good (suitable) processing as an endoscope image by changing amplitude of a dynamic range of a digital video signal according to a kind of an endoscope to be used.

BEST MODE FOR CARRYING OUT THE INVENTION

Embodiments of the present invention will be described with referring to drawings.

First Embodiment

Figure 1:
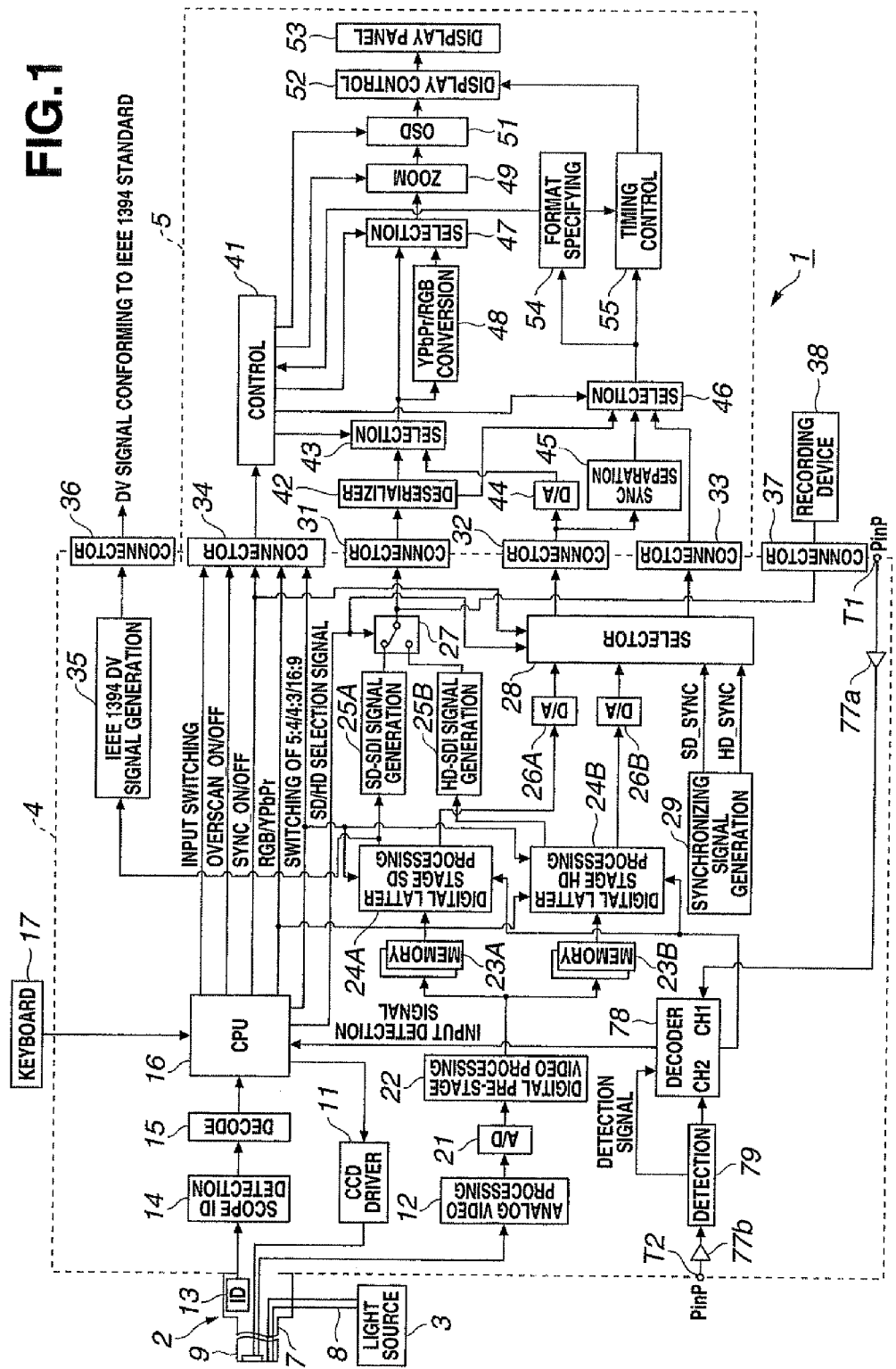
FIG. 1 is a block diagram illustrating a whole configuration of an endoscope system equipped with an endoscope apparatus of the present invention.

FIG. 1 illustrates a whole configuration of an endoscope system equipped with an endoscope apparatus of the present invention.

An endoscope system 1 illustrated in FIG. 1 is equipped with an endoscope (abbreviated as a scope) 2 which is inserted into a body cavity, picks up an image of a test location with an image pickup section including a solid state image pickup element, and outputs an image pickup signal, a light source 3 which supplies illumination light to the scope 2, a video processor 4 as a signal processing apparatus for an endoscope which performs signal processing to an image pickup signal from the image pickup section to which a signal connector of the scope 2 is connected detachably, and which is mounted in the scope 2, a monitor 5 which displays an endoscope image picked up in the image pickup section by a video signal being input through connectors 31 to 34 which are connected to the video processor 4 detachably, and a storing device 38 which stores an endoscope image picked up in the image pickup section by a video signal being input through a connector 37 connected detachably to the video processor 4. The endoscope apparatus is configured of the scope 2, light source 3, and video processor 4.

In FIG. 1, various kinds of CCDs 9 are mounted in the scope 2, and hence, the video processor 4 to which the scope 2 is connected detachably can perform signal processing corresponding to the various kinds of CCDs 9. Thus, in FIG. 1, although one scope 2 is illustrated, two or more kinds of scopes in which pixel counts (resolutions) of the CCDs 9 are different are connected to the video processor 4 and are used actually.

As the CCDs 9 in this case, as a typical example, there are those having pixel counts respectively corresponding to two kinds of video signals, an SDTV signal (standard image signal) and an HDTV signal (e.g., a high definition video signal).

Then, the video processor 4 is equipped with a function to perform signal processing, which generates SDTV, and signal processing, which generates HDTV, according to the CCDs 9 mounted in the scope 2. In addition, also in the case of a CCD 9 corresponding to HDTV, a modified example mentioned later is equipped with a function of converting it into SDTV and outputting it, and can also output it in the SDTV.

In addition, corresponding to the video processor 4 equipped with the function of signal processing which generates SDTV and HDTV, the monitor 5 is equipped with a function to a display corresponding to any signal aspect of the SDTV and HDTV.

In this case, in the present embodiment, by enabling an output of SDTV and HDTV video signals, whose resolutions are different, to the monitor 5 from the common connectors 31 and 32 as mentioned later, it is made not only to improve operability by making connection work simple, but also to achieve it in a small space.

In addition, by inputting an instruction such as a signal aspect from a keyboard 17 as an information inputting section, a user sends a remote signal as control information corresponding to the instruction input to a monitor 5 side from the video processor 4 to be able to perform remote control of display process in the monitor 5 side with corresponding to the instruction input as described below.

The above-mentioned scope 2 has a slender insertion section 7 inserted into a body cavity, a light guide 8 which transmits illumination light is inserted in the insertion section 7, and illumination light is incident into an incident end face of a rear end of the light guide 8 from the light source 3. The light guide 8 transmits the incident illumination light, emits it from an end surface of the light guide installed in an illumination window of an end section of the insertion section 7, and illuminates a subject such as an affected part.

An objective lens which is not illustrated is installed in an observation window which is provided adjacently to the illumination window, for example, a charge coupled device (abbreviated as CCD) 9 is arranged as a solid state image pickup element in its image forming position, and the CCD 9 performs photo-electric conversion of an optical image which is imaged on an image pickup plane. CCDs respectively corresponding to SDTV and HDTV are used for the CCD 9 mounted in the scope 2. In addition, there is also a case that they are CCDs corresponding to both by adopting a form of superimposing a control signal, corresponding to an image by the CCD 9, on a part in a video signal in the SDTV or HDTV.

By a signal connector of the scope 2 being connected to the video processor 4, a CCD driver 11 provided in the video processor 4 applies a CCD drive signal to the CCD 9. The CCD 9 outputs a CCD output signal, which is given photo-electric conversion by the application of the CCD drive signal, to an analog video processing circuit 12 in the video processor 4.

In addition, a scope ID generating circuit (in FIG. 1, it is abbreviated as ID) 13 as an information inputting section which generates an ID code unique to the scope 2 is built-in each scope 2. Then, the scope ID code is read by a scope ID detecting circuit 14 of the video processor 4, and further, information decoded through a decode circuit 15 is input into a CPU 16 which controls each section in the video processor 4.

With responding to the ID code from the scope ID generating circuit 13 and the instruction input from the keyboard 17, the CPU 16 controls drive of the CCD driver 11 which drives the CCD 9 built in the scope 2, and controls each section of a signal-processing system which performs signal processing to the CCD output signal. In addition, in the case of a scope which does not have the scope ID generating circuit 13, it is also possible to instruct and set the processing corresponding to the CCD 9, built in the scope, from the keyboard 17 provided in the external of the video processor 4.

This keyboard 17 is connected to the CPU 16 inside the video processor 4, and at the time of endoscopy, a user can control each section inside the video processor 4 by inputting patient information from the keyboard 17, or inputting a control command to the CPU 16. In addition, it is made not only to be able to control each section of the video processor 4, but also to perform remote control of the monitor 5 by outputting a remote control signal which instructs a signal aspect of a video signal to the monitor 5 connected to the video processor 4.

After amplification, correlation double sampling processing and the like are preformed by the analog video processing circuit 12, the above-mentioned CCD output signal is input into the A/D conversion circuit 21 to be converted into a digital signal from an analog signal.

This digital signal is input into a digital pre-stage video processing circuit 22 to be given color separation processing of separating it into a luminance signal and a chrominance signal, matrix processing of converting it into RGB signals from the luminance signal and the chrominance signal, white balance processing and the like, and thereafter is temporarily stored in two memory blocks 23A and 2313. The signals read from these two memory blocks 23A and 23B are given signal processing corresponding to a standard video signal (abbreviated as SDTV or just SD) and a high definition video signal (abbreviated as HDTV or just HD), which resolution is far high than the SDTV, as described below.

The signal read from the memory block 23A is input into a digital post-stage SD processing circuit 24A to be given expanding processing, enhancing processing, and the like based on the SDTV in the digital post-stage SD processing circuit 24A. Then, an output signal of the digital post-stage SD processing circuit 24A is input into an SD-SDI signal generating section 25A, which converts it into a serial video signal, and a D/A conversion circuit 26A. The SD-SDI signal generating section 25A has a serial digital interface (SDI), and converts a digital SDTV into a (digital) serial video signal.

In addition, a signal read from the memory block 23B is input into a digital post-stage HD processing circuit 24B. Then, in the digital post-stage HD processing circuit 24B, expanding processing, enhancing processing, and the like based on the HDTV are performed.

The digital post-stage SD processing circuit 24A and the digital post-stage HD processing circuit 24B perform the processing corresponding to respective aspect ratios since the aspect ratios of the SD and the HD are different.

Then, an output signal of the digital post-stage HD processing circuit 24B is input into an HD-SDI signal generating section 25B, which converts it into a serial video signal, and a D/A conversion circuit 26B.

The serial output signals of the SD-SDI signal generating section 25A and the HD-SDI signal generating section 25B are input into the monitor 5 from the digital video connector (digital video terminal) 31 through a change-over switch 27.

In the changeover switch 27, one serial video signal which is switched to be selected by an SD/HD selecting signal output from the CPU 16 by an SD or HD selection instruction with, for example, the keyboard 17 is input into the monitor 5 from the digital video connector 31.

In addition, analog SDTV and HDTV video signals converted by the D/A conversion circuits 26A and 26B are input into the monitor 5 from the analog component video connector (analog component video terminal) 32 through the selector 28.

In addition, SDTV and HDTV synchronized signals, i.e., SD_SYNC and HD_SYNC are input into the selector 28 from a synchronizing signal generating circuit 29. Then, these synchronizing signals SD_SYNC and HD_SYNC can be also input into the monitor 5 through the connector 33 for a synchronizing signal (terminal for a synchronizing signal) from the selector 28.

In addition, an input switching signal from the CPU 16, and the like are also input into the monitor 5 through a remote connector (remote terminal) 34.

Here, configuration of the above-mentioned selector 28 will be described simply.

RGB signals of the SD and the HD are input through a three-input changeover switch (not illustrated) into the monitor 5 from the analog component video connector 32. In addition, the synchronizing signals SD_SYNC and HD_SYNC are input into the monitor 5 from the connector 33 for a synchronizing signal through a two-input changeover switch (not illustrated).

The above-mentioned three-input changeover switch and the above-mentioned two-input changeover switch in the selector 28 are switched with being linked with the SD/HD selecting signal.

In addition, the synchronizing signal HD_SYNC is not only added to a G signal of the HD by an adder (not illustrated) but also input into one input terminal of the above-mentioned two-input changeover switch through a buffer (not illustrated).

It is made to be able to input the synchronizing signal SD_SYNC or the HD_SYNC in the video processor 4 through the connector 33 for a synchronizing signal to the monitor 5 (as an external synchronizing signal), or instead, to be able to take in a video signal from the analog component video connector 32, and also to use the synchronizing signal superimposed on the video signal with performing separation of the synchronizing signal.

As illustrated in FIG. 1, in the video processor 4, terminals T1 and T2 for picture-in-pictures (abbreviated as PinP) are provided in a rear panel and a front panel, respectively, and a signal input from the terminal T1 is input into a channel CH1 of a decoder 78 through a buffer 77a.

In addition, a signal input from the terminal T2 is input into a channel CH2 of the decoder 78 through the buffer 77b and a detecting circuit 79 which detects a signal.

Then, it is made not only to be able to output also the video signal input from either of the terminals T1 and T2 as a video signal displaying it in PinP, but also not only to display, for example, the video signal input from the terminal T2 in PinP in preference by the detecting circuit 79.

Thus, it is made to be able to perform processing of display in PinP by the detecting circuit 79 outputting a detection signal to the decoder 78 when a signal is input from the terminal T2, and the decoder 78 outputting the signal input from the CH2 in preference by the detection signal output from the terminal 2 to give priority to the digital post-stage SD processing circuit 24A or the digital post-stage HD processing circuit 24B.

In addition, the decoder 78 outputs an input detection signal to the CPU 16, and by the signal, the CPU 16 sends a control signal to the digital post-stage SD processing circuit 24A or the digital post-stage HD processing circuit 24B to perform control of making PinP processing performed.

In addition, as illustrated in FIG. 1, in the remote connector 34, remote signals are input into the monitor 5 from the CPU 16 of the video processor 4.

As these remote signals, there are a switching signal which switches video signals (SDTV and HDTV) input into the monitor 5 (output in view from the video processor 4 side), an OVERSCAN_ON/OFF signal, a SYNC_ON/OFF signal, an RGB/YPbPr switching, and an aspect switching signal (specifically, a 5:4/4:3/16:9 switching signal).

These remote signals are input into a control circuit 41 inside the monitor 5 through the remote connector 34, and the control circuit 41 is linked with the remote signals to control each section in the monitor 5.

The digital serial video signal input into the above-mentioned digital video connector 31 is input into a selecting circuit 43 through a deserializer 42 converting a serial video signal into a parallel video signal (specifically, a YPbPr signal).

In addition, analog component video signals input from the analog component video connector 32, i.e., RGB signals in SDTV, and HDTV are converted into digital signals by an A/D converter 44, and are input into the selecting circuit 43. In this case, in the case of HDTV, a synchronizing signal which is superimposed on a G signal is separated and extracted by a sync separation circuit 45 to be input into a selecting circuit 46.

In addition, the synchronizing signal separated is input into the selecting circuit 46 from the deserializer 42.

The digital video signal selected by the selecting circuit 43 is not only further input into the selecting circuit 47, but also input into the selecting circuit 47 through a YPbPr/RGB conversion circuit 48 converting into RGB signals from the YPbPr signal as a Y/color difference component signal. In addition, Pb and Pr signals are also called a B-Y signal and an R-Y signal, respectively.

The signal selected by the selecting circuit 47 is input into an onscreen display unit (OSD) circuit 51 through a zooming circuit 49 which performs enlargement or shrinkage. The OSD circuit 51 is a circuit of performing processing of superimposing and displaying a graphic image such as a menu, on an endoscope image which is displayed on a screen of a display panel 53, and which is zoomed.

ON/OFF of screen display by the OSD circuit 51, selection of the selecting circuits 43, 46, and 47, and the enlargement/shrinkage by the zooming circuit 49 are controlled by the control circuit 41.

An output signal of the OSD circuit 51 is input into the display panel 53, which is configured of a display section such as a liquid crystal display, through a display control circuit 52 which performs display control process, and the endoscope image, which is picked by the CCD 9, and the like are displayed on the display panel 53.

In addition, the synchronizing signal selected by the selecting circuit 46 is input into a format specifying circuit 54 which performs format specification (determination) of SDTV/HDTV, and a timing control circuit 55 which performs timing control.

The format specifying circuit 54 sends information on a format of one, which is specified out of SDTV and HDTV, to the control circuit 41 and the timing control circuit 55, and the control circuit 41 performs control corresponding to the specified format.

In addition, the timing control circuit 55 sends a timing signal corresponding to the specified format to the display control circuit 52, and the display control circuit 52 performs display control process, corresponding to the specified format, to the video signal of the endoscope.

In addition to the above configuration, the endoscope system 1 is equipped with an IEEE 1394 DV signal generating circuit 35, which inputs an SDTV signal which is given enlargement processing, enhancement processing, and the like by the digital post-stage SD processing circuit 24A, and generates a signal in a DV format of the IEEE 1394 telecommunications standard (thus, a DV signal on the IEEE 1394 standard), in the video processor 4, and hence, it is in such configuration that can supply a DV signal on the IEEE 1394 standard through a connector 36 to an external device which conforms to the IEEE 1394 standard but is not illustrated.

Furthermore, in FIG. 1, it has such configuration that serial output signals of the SD-SDI signal generating section 25A and the HD-SDI signal generating section 25B are switched in the changeover switch 27 with the SD/HD selecting signal output from the CPU 16, and one of the serial video signals which is switched and selected then is output to the storing device 38 from the connector 37.

Figure 2:
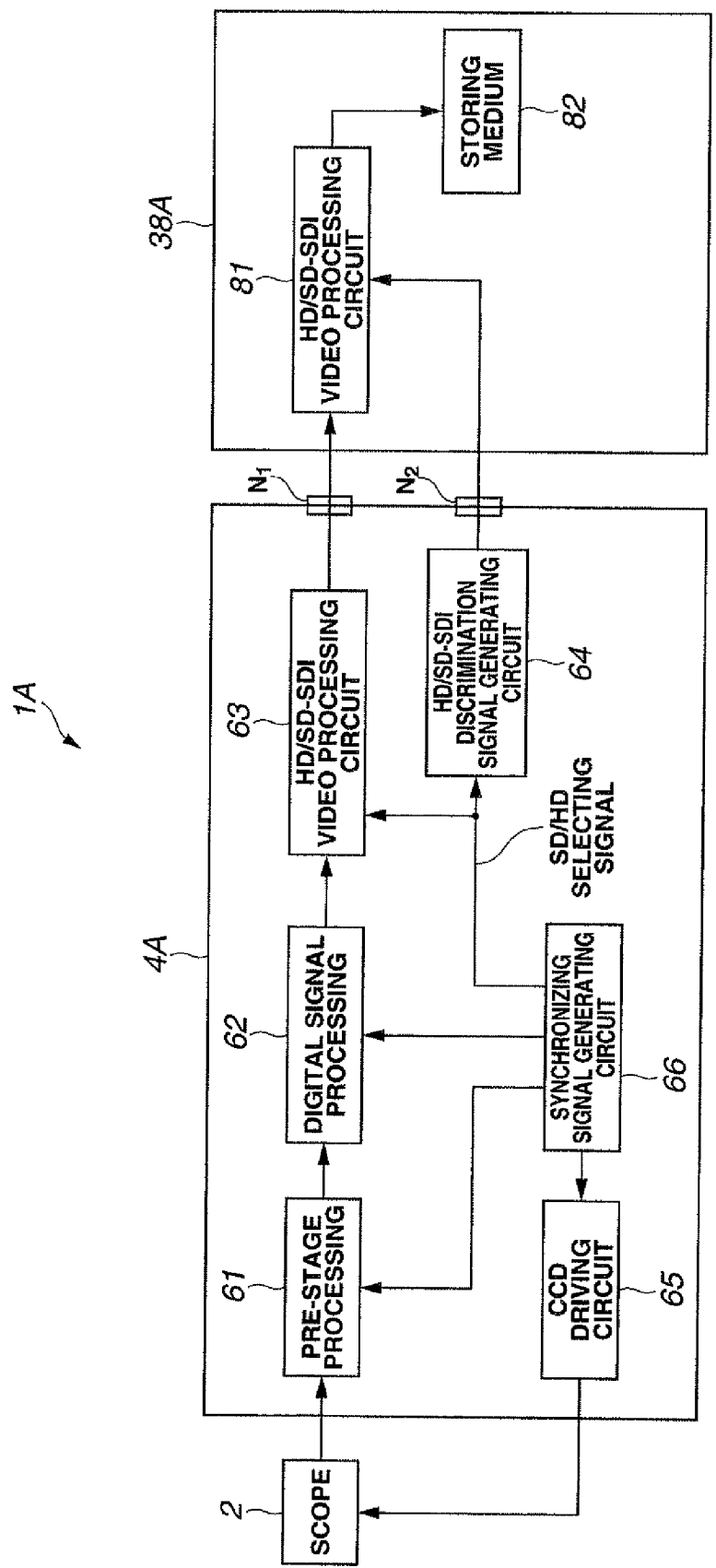
FIG. 2 is a block diagram illustrating a schematic whole configuration of an endoscope system equipped with an endoscope apparatus of a first embodiment of the present invention.

FIG. 2 illustrates schematic whole configuration of an endoscope system equipped with an endoscope apparatus of the first embodiment of the present invention. Nevertheless, the light source 3 and the monitor 5 which illustrated in FIG. 1 are omitted. In addition, only an output system of the digital video signals in FIG. 1 is illustrated, and an analog video signal output system is omitted.

In FIG. 2, an endoscope system 1A comprises a scope 2 which is inserted into a body cavity, picks up an image of a test location by an image pickup section which corresponds to HDTV and/or SDTV and uses a solid state image pickup element, and outputs an image pickup signal, a video processor 4A which performs signal processing to an image pickup signal picked up in the scope 2, and a storing device 38A which stores a signal of an endoscope image, picked up by the image pickup section, with being linked with switching by a video processor 4A side by a video signal being input through a connector N1 (equivalent to the reference numeral 37 in FIG. 1) for storing device connection as a first connector from a video processor 4A, and simultaneously, an HDTV/SDTV discrimination signal being input through a connector N2 as a second connector.

A CCD as a solid state image pickup element which outputs an image pickup signal is built in the scope 2.

The video processor 4A is equipped with a pre-stage processing circuit 61, a digital signal processing circuit 62 as a digital converting section, an HD/SD-SDI video processing circuit 63 as a video signal generating section, an HD/SD-SDI discrimination signal generating circuit 64 as a discrimination signal generating section, a CCD driving circuit 65, and a synchronizing signal generating circuit 66.

After performing A/D conversion of an HDTV or SDTV image pickup signal from the scope 2 to obtain a digital video signal, the pre-stage processing circuit 61 performs pre-stage processing such as color separation processing, matrix processing, and white balance processing.

The digital signal processing circuit 62 as a digital converting section in the present embodiment performs enlargement processing, enhancement processing, and the like of the HDTV or SDTV digital video signal which conform to the HDTV or SDTV.

The HD/SD-SDI video processing circuit 63 as a video signal generating section in the present embodiment converts the HDTV or SDTV digital video signal into a serial digital video signal (it is called an HD-SDI signal or an SD-SDI signal, respectively) of serial HDTV or SDTV, and selectively switches the serial digital video signal (HD-SDI signal or SD-SDI signal) into one serial digital video signal with an SD/HD selecting signal as a selection instruction from the synchronizing signal generating circuit 66 to output it. The HD-SDI is abbreviation for High Definition Serial Digital Interface, and the SD-SDI is abbreviation for Standard Definition Serial Digital Interface.

The HD/SD-SDI discrimination signal generating circuit 64 as a discrimination signal generating section in the present embodiment inputs the SD/HD selecting signal from the synchronizing signal generating circuit 66, and generates an HD/SD-SDI discrimination signal for a storing device (38A) at the almost same time (without almost generating time delay) when the SD/HD selecting signal is input.

The CCD driving circuit 65 supplies a drive signal to a CCD in the scope 2 to drive the CCD.

The synchronizing signal generating circuit 66 generates an operation clock and an SD/HD selecting signal, and supplies them to the pre-stage processing circuit 61, the digital signal processing circuit 62, the CCD driving circuit 65, the HD/SD-SDI video processing circuit 63, and the HD/SD-SDI discrimination signal generating circuit 64.

The storing device 38A is equipped with an HD/SD-SDI video processing circuit 81 as a signal processing section, and a storing media 82 such as a memory card.

The HD/SD-SDI video processing circuit 81 as a signal processing section in the present embodiment inputs the HD-SDI signal or SD-SDI signal which is sent through the first connector N1 from the HD/SD-SDI video processing circuit 63 in the video processor 4A and which is a serial digital video signal, and copes with switching to the HD-SDI signal or the SD-SDI signal using the HD/SD-SDI discrimination signal for a storing device sent through the second connector N2 from the HD/SD-SDI discrimination signal generating circuit 64 in the video processor 4A after performing serial/parallel conversion and separating it into a luminance signal and color-difference signals to perform conversion processing to RGB signals according to each SDI signal, and storage control such as compression processing necessary for storage.

Here, the HD/SD-SDI discrimination signal for a storing device means to be a signal form readable in the storing device 38A. Hence, the HD/SD-SDI video processing circuit 81 is switched with coping with the discrimination signal, and can execute video processing.

The storing medium 82 stores a compression signal from the HD/SD-SDI video processing circuit 81, and may be a medium such as an optical disk such as a DVD, and a magnetic disk such as a hard disk besides semiconductor memory such as a memory card.

In the endoscope system 1A including the endoscope apparatus (2, 4A) configured as described above, the video processor 4A which is a processor processes an image pickup signal from a CCD to generate an HD-SDI signal and an SD-SDI signal, which are switched selectively and serial output to a storing device 38A side through the first connector N1 (it is the same as the connector 37 in FIG. 1). On the other hand, the video processor 4A is equipped with the HD/SD-SDI discrimination signal generating circuit 64, and the HD/SD-SDI discrimination signal generating circuit 64 is linked with the above-mentioned selection switching of the HD-SDI signal or the SD-SDI signal, and generates the HD/SD-SDI discrimination signal with which it can be discriminated whether it is the HD-SDI signal and whether it is the SD-SDI signals. In addition, the HD/SD-SDI discrimination signal is synonymous with the HDTV/SDTV discrimination signal. This HD/SD-SDI discrimination signal is output to the storing device 38A side through the second connector N2 different from the first connector N1.

In the storing device 38A, the HD/SD-SDI video processing circuit 81 inputs the HD-SDI signal or the SD-SDI signal selectively switched and output from the first connector N1, performs signal processing corresponding to the above-mentioned input HD-SDI signal or SD-SDI signal using the HD/SD-SDI discrimination signal output from the second connector N2, and performs storage on the storing medium 82.

According to the present first embodiment, since the HD/SD-SDI discrimination signal in the signal form which meets specifications of the storing device 38A is generated to the video processor 4A side and supplies it to the HD/SD-SDI video processing circuit 81 in the storing device 38A through the second connector N2, switching of video storage of the HD-SDI signal and SD-SDI signal in the storing device 38A is performed in an instant with almost synchronizing with selection switching in the HD/SD-SDI video processing circuit 63 inside the video processor 4A, and hence, a period when a recorded video image stops hardly arises. In short, by picking up an image using a solid state image pickup element mounted in an endoscope inserted in an inside of a body, performing signal processing of generating an SDTV signal or a HDTV signal from the image pickup signal, enabling an output of the generated SDTV signal or HDTV signal from a first connector, and also making recording processing and display processing operated in an external device into which a video signal is input with being linked with the output without a time lag, lack in a stored video image or a display video hardly arises.

Second Embodiment

Figure 3:
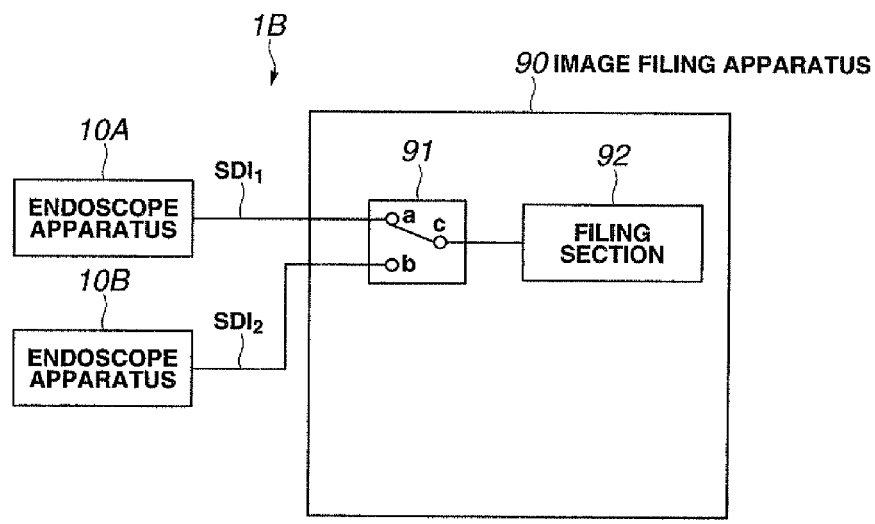
FIG. 3 is a block diagram illustrating a schematic whole configuration of an endoscope system of a second embodiment of the present invention.

FIG. 3 illustrates schematic whole configuration of an endoscope system of a second embodiment of the present invention.

In FIG. 3, it is made that an endoscope system 1B has such configuration that two or more endoscope apparatuses (two sets in the figure) 10A and 10B are prepared, and serial digital video signals SD11 and SD12 from these endoscope apparatuses 10A and 10B are filed (stored) in a filing section 92 of an image filing apparatus 90.

The image filing apparatus 90 is equipped with a switching circuit 91 which is a selection section which inputs serial digital video signals SD11 and SD12 from the endoscope apparatuses 10A and 10B into input terminals a and b, switches these inputs selectively, and outputs it to an output terminal c, and a filing section 92 which files either of the serial digital video signals SD11 and SD12 which is switched selectively by the CPU 16 on the basis of an instruction by an operation section, and the like in the switching circuit 91.

Here, there was a possibility of filing accidentally a serial digital video signal from an endoscope apparatus, which was not intended, when the switching circuit 91 malfunctioned. Then, in the second embodiment, by inserting a MAC address of Ethernet (registered trademark) which is data unique to each encloseope apparatus in a blanking period of a video in a serial digital video signal, even when the plurality of endoscope apparatuses 10A and 10B is SDI-connected in the image filing apparatus 90, it is possible to specifies securely the endoscope apparatus filed now in an image filing apparatus 90 side from the MAC address of the filed serial digital video signal.

In addition, the MAC address is abbreviation for Media Access Control address, and means an ID number unique to each Ethernet (registered trademark) card. A number unique to each is assigned to each global Ethernet (registered trademark) card, and transmission and reception of data between cards are performed on the basis of this. It is expressed by combining a number unique to each manufacturer which is managed and assigned by IEEE, and a number which the manufacturer assigns uniquely to each card.

With following this, besides insertion of MAC addresses (unique identification information) of Ethernet (registered trademark) in video blanking periods of the serial digital video signals SD11 and SD12, it is also acceptable to further insert additional information which becomes useful at the time of endoscope observation. For example, information on a connected scope and a function in use as shown below is cited.

Serial number of a scope connected to an endoscope apparatus

Kind of a CCD of the scope connected to the endoscope apparatus

Whether the scope connected to the endoscope apparatus corresponds to infrared observation Whether it is made to operate presently in an infrared observation mode in the case of correspondence to the infrared observation Whether the scope connected to the endoscope apparatus can correspond to NBI (Narrow Band Imaging)

Whether it is displayed presently in an NBI mode in the case of correspondence to the NBI Patient's ID These information can be input using the keyboard 17 (refer to FIG. 1), the scope ID generating circuit 13, or the coefficient switching section 102 mentioned later as an information inputting section.

How to input the information in a video blanking period is to insert it into auxiliary data standardized by SMPTE292M (standard of HD-SDI) in the case of an HD-SDI signal or SMPTE259M (SD-SDI standard) in the case of an SD-SDI signal. In each standard, inserting auxiliary data in a blanking period other than a video is accepted (voice data, a time code, and the like are stored in the portion as the auxiliary data), and user data words (UDW) which a user or a manufacturer may use freely is also defined. The above-mentioned information useful for the endoscope apparatus is stored in the user data words.

Figure 4:
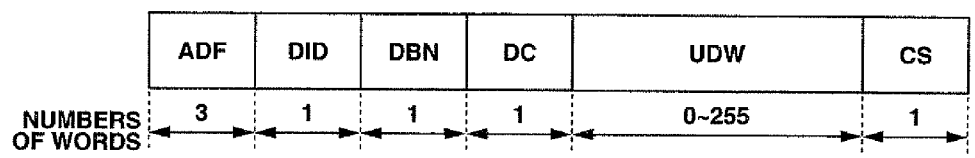
FIG. 4 is a diagram illustrating a first form of an auxiliary data configuration in a video blanking period which relates to the second embodiment of the present invention and is standardized by an HD-SDI standard, or an SD-SDI standard.
Figure 5:
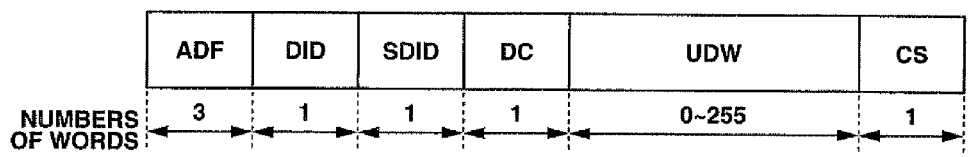
FIG. 5 is a diagram illustrating a second form of an auxiliary data configuration in a video blanking period which relates to the second embodiment of the present invention and is standardized by the HD-SDI standard, or the SD-SDI standard.

FIGS. 4 and 5 illustrate the configuration of the auxiliary data in a video blanking period standardized by the HD-SDI standard, or the SD-SDI standard. FIG. 4 illustrates a first form of auxiliary data configuration, and FIG. 5 illustrates a second form of the auxiliary data configuration. In these Figs., ADF denotes an auxiliary data flag, DID denotes a data identification word, DBN denotes a data block number, SDID denotes a second data identification word, DC denotes a data count word, UDW denotes a user data word(s), and CS denotes a checksum word.

According to the present second embodiment, when serial digital video signals from a plurality of endoscope apparatuses are switched selectively and filed, even if a malfunction arises in a switching (selection) section, it is possible to specify an endoscope apparatus, which is a video source, correctly from a MAC address included in a filed serial digital video signal. Hence, it becomes possible to solve an issue of a wrong patient which should be avoided as medical equipment.

Third Embodiment

Figure 6:
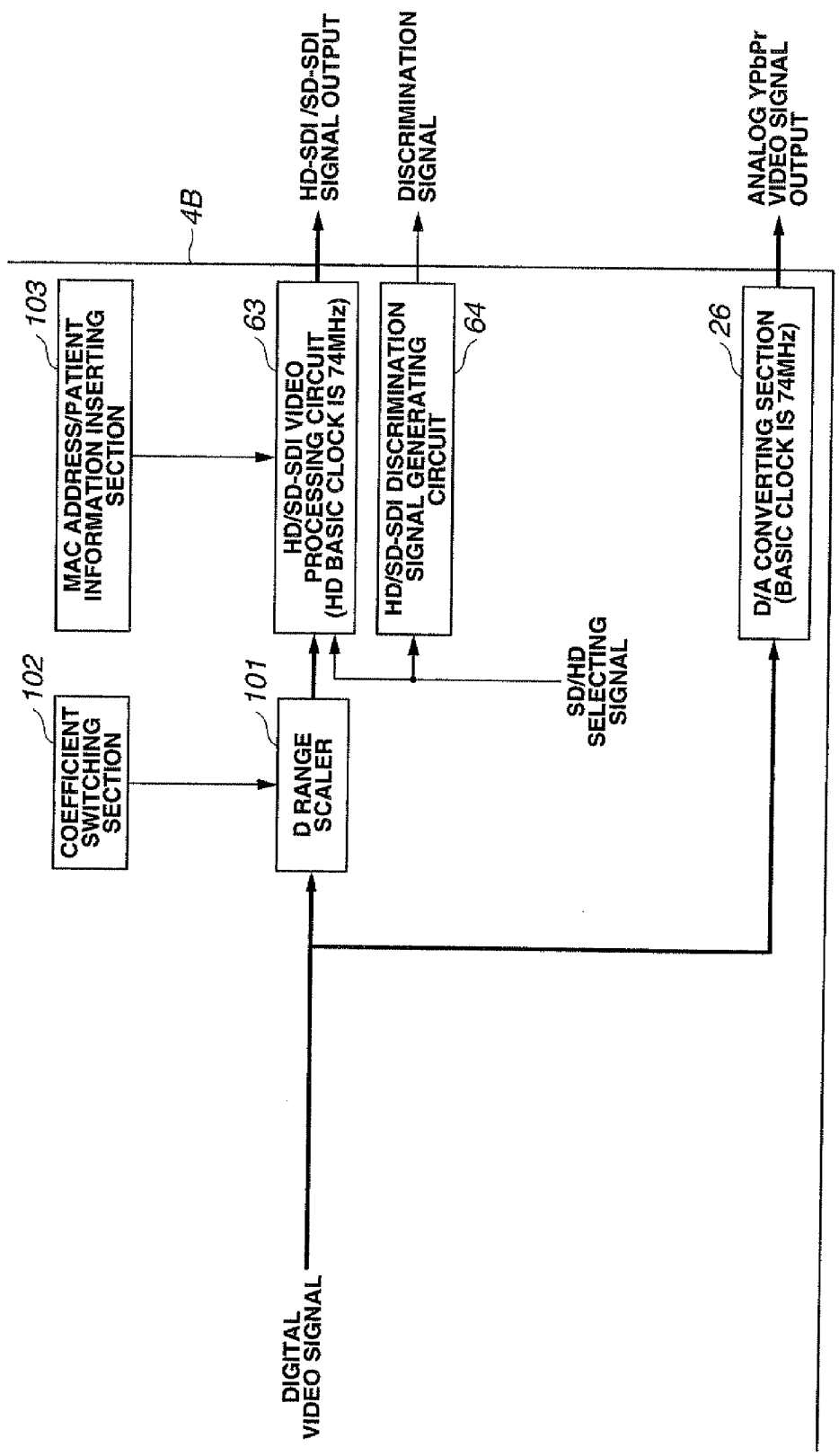
FIG. 6 is a block diagram illustrating a configuration at the time of an HDTV output in configuration of a final video output portion of a video processor in an endoscope apparatus of a third embodiment of the present invention.
Figure 7:
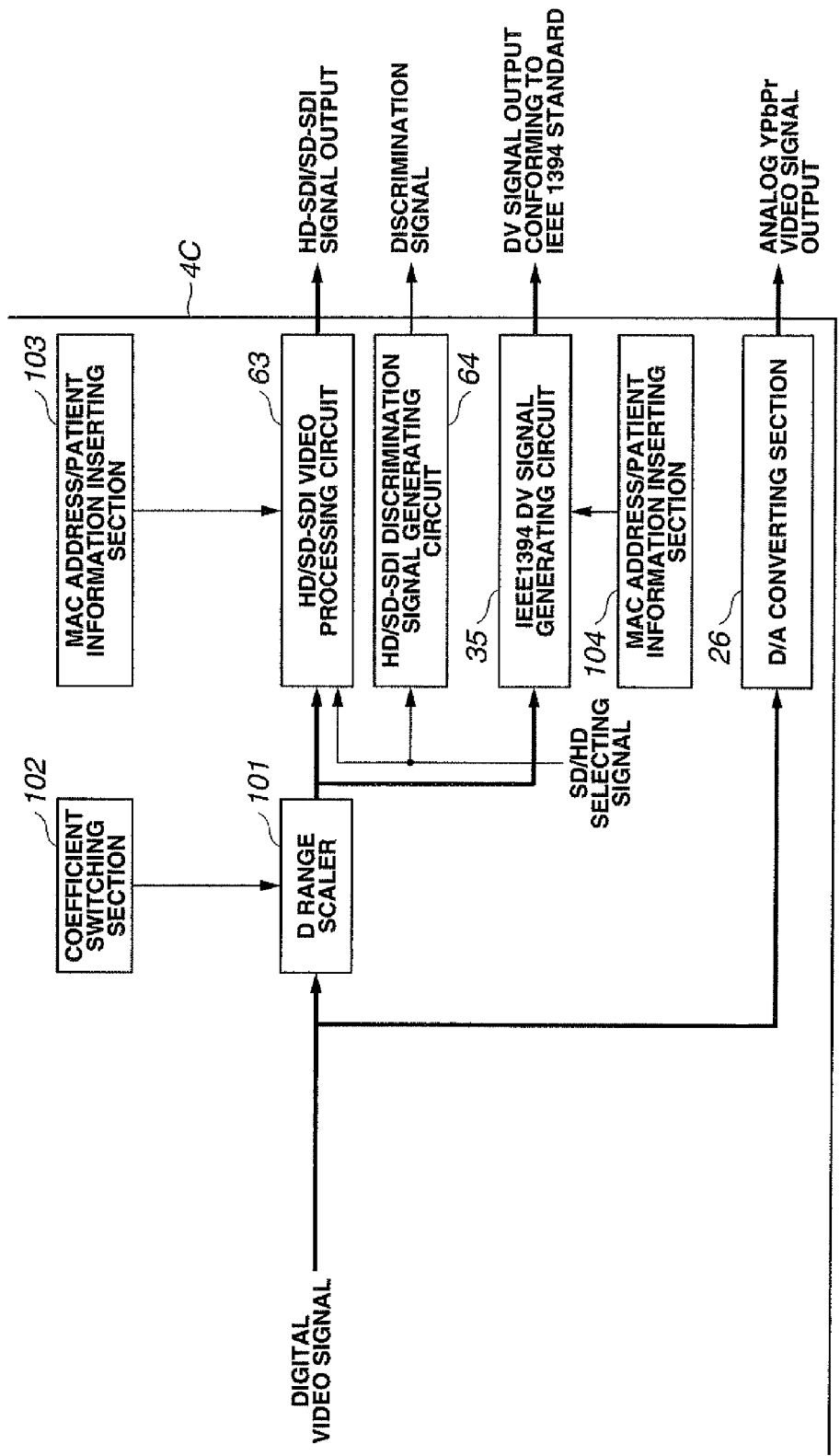
FIG. 7 is a block diagram illustrating a configuration at the time of an SDTV output in configuration of a final video output portion of a video processor in the endoscope apparatus of the third embodiment of the present invention.

FIGS. 6 and 7 illustrate the configuration of a final video output section of a video processor in an endoscope apparatus of a third embodiment of the present invention. FIG. 6 illustrates the configuration at the time of an HDTV output, and FIG. 7 illustrates the configuration at the time of an SDTV output. These figures illustrate sections which performs generation and output of a serial digital video signal HD-SDI signal or SD-SDI signal of the video processor 4B (or 4C) in the endoscope system. Hence, FIG. 6 has the configuration in which the IEEE 1394DV signal generating circuit 35 in FIG. 7 is omitted. The same or similar reference numerals will be assigned to the same parts as those in FIGS. 2 and 1, and will be described.

In FIG. 6, as described above, the HD/SD-SDI video processing circuit 63 inputs an HDTV or SDTV digital video signal from the digital signal processing circuit 62 (refer to FIG. 2) which is a preceding stage of digital converting section and which is not illustrated, converts it into an HD-SDI signal or an SD-SDI signal which is a serial HDTV or SDTV digital video signal, switches selectively the HD-SDI signal or SD-SDI signal to one serial digital video signal (HD-SDI signal or SD-SDI signal) using the SD/HD selecting signal from the synchronizing signal generating circuit 66 (refer to FIG. 2) which is not illustrated, and outputs it. At that time, as described in FIG. 2, the HD/SD-SDI discrimination signal generating circuit 64 generates and outputs the HD/SD-SDI discrimination signal for the storing devices 38A (refer to FIG. 2) which is externally connected to the video processor 4B, and which is not illustrated.

Then, a dynamic range scaler (abbreviated as a D range scaler) 101 as a dynamic range converting section is arranged between the HD/SD-SDI video processing circuit 63 and the digital signal processing circuit 62 (refer to FIG. 2) which is its preceding stage, and which is not illustrated.

While a digital video signal from the digital signal processing circuit 62 (refer to FIG. 2) which is a preceding stage, and which is not illustrated is supplied to the D range scaler 101, it is given D/A conversion in the D/A converting section 26 as it is, and is output as analog video signals (a luminance signal Y and color-difference signals Pb and Pr). Here, Pb and Pr signals are also called a B-Y signal and an R-Y signal, respectively. In addition, a basic clock in the HD/SD-SDI video processing circuit 63 and the D/A converting section 26 is 74 MHz. This is because an HDTV basic clock (driving clock) of the monitor 5 connected to a post-stage of the video processor 4B is generally specified at 74 MHz.

The coefficient switching section 102 as an information inputting section is connected to the D range scaler 101 as a dynamic range converting section in the present embodiment, and it is made to be able to change amplitude of a dynamic range so as to be able to observe an endoscope image in a better state in each case by switching a dynamic range transform coefficient (scaling factor) in the coefficient switching section 102 by destination (e.g., distinction between U.S.A. and Europe) in use or by type of the scope to be used (e.g., by scope having a CCD at different resolution).

In addition, for the HD/SD-SDI video processing circuit 63, similarly as described in FIG. 3, it is possible to improve reliability of the data and to improve convenience, at the time of outputting it to an image filing apparatus and a storing device which are not illustrated by inserting a MAC address as a specific identification number, and patient information, such as a patient ID, in a video blanking period of a serial digital video signal (HD-SDI signal or SD-SDI signal) by the MAC address/patient information insertion section 103 as an additional information insertion section.

In FIG. 7, a different point from FIG. 6 is that the SDTV digital video signal which is given dynamic range conversion in the D range scaler 101 is supplied to not only the HD/SD-SDI video processing circuit 63 but also the IEEE 1394DV signal generating circuit 35 at the time of an SDTV output, and a DV signal on the IEEE1394 standard is output to the external of the video processor 4C.

As for the IEEE1394 DV signal generating circuit 35, since the DV signal on the IEEE1394 standard is also a serial digital video signal, it is possible to improve reliability of the data and to improve convenience, at the time of outputting it to an image filing apparatus and a storing device which are not illustrated by inserting a MAC address as the specific identification number, and patient information, such as a patient ID, in a video blanking period of a serial digital video signal, which is an IEEE1394 DV signal by the MAC address/patient information insertion section 104 as the additional information insertion section.

When a video signal which is given digital processing in the video processor 4B (4C) configured as the above is displayed on the monitor 5, the video processor prepares an analog video signal and digital video signals (=HD-SDI, SD-SDI, and DV signals) as outputs.

As for the analog video signal to be output, when an input digital video signal is an 8-bit system, D/A conversion of a full scale of 0 to 255 is performed as it is, and it is output as the analog video signal.

On the other hand, as for the digital video signal to be output, it is recommended as a digital video output to perform scaling transformation of a digital level and to output a luminance signal Y at 16 to 235, and color-difference signals Cb/Cr in a narrow dynamic range of 16 to 240. When performing such scaling transformation, there is a defect of becoming an endoscope image deficient in tone when masking upper and lower sides of an 8-bit digital video signal as it is. Then, dynamic range conversion is performed using the following formula to make it possible to use a dynamic range of the digital level effectively.

Case of Y signal(220 gradations/256 gradations)× video signal(Y)

Case of CbCr signals(225 gradations/266 gradations)× video signal(Cb/Cr)

In addition, depending on a kind of the scope 2 connected to a video processor, in other words, depending on a field (there are a lot of ones such as upper portion/lower portion endoscopies, and a laparoscope surgery) to be used, there is a case that it is more attractive in image quality at the time of viewing a monitor screen to set up a pedestal level (black level used as a reference) (that is, a predetermined value is added to the reference level which is a lower level in a dynamic range).

For example, a set up level is set to 8, Also in this case, without masking upper and lower parts of the 8-bit digital video signal as it is, scaling is performed as the following formula.

Case of Y signal(212 gradations/256 gradations)× video signal(Y)

Thereby, it is possible to obtain an attractive image in image quality.

In addition, although it has been performed conventionally to give dynamic range conversion to a digital video output by a D range scaler, changing dynamic ranges of an analog video output and a digital video output has not been performed in an endoscope apparatus. This is because there is no endoscope apparatus which has both outputs of an analog video output and a digital video output in a video processor. In addition, changing a set up level every scope to make a dynamic range of a digital video output variable has not been performed in conventional endoscope apparatuses. Nevertheless, changing a dynamic range according to a destination such as an NTSC system and a PAL system has been already performed. Hence, by changing a dynamic range by scope and by destination, or by destination and by scope, it is possible to obtain an image more suitable to customer's needs.

Fourth Embodiment

Figures 8, 9:
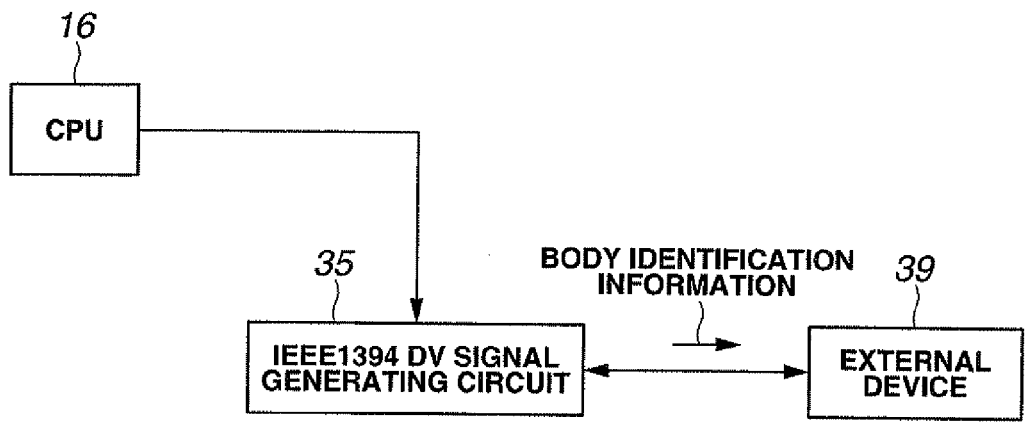
FIG. 8 is a drawing illustrating a configuration of an IEEE 1394 identification number in an endoscope apparatus of a fourth embodiment of the present invention.
FIG. 9 is a block diagram describing a setting method of the IEEE 1394 identification number in the endoscope apparatus of the fourth embodiment of the present invention.

FIGS. 8 and 9 illustrate configuration of an IEEE 1394 identification number, its setup, and operation after the setup in an endoscope apparatus of a fourth embodiment of the present invention. FIG. 8 illustrates the configuration of the IEEE 1394 identification number, and FIG. 9 illustrates a block diagram of a setup method of the IEEE 1394 identification number.

It is standardized in the IEEE 1394 to set a unique identification number (64 bits) every body as identification information of the body.

As illustrated in FIG. 8, as for the configuration of the identification number, upper 24 bits denote a vendor ID assigned every vendor, and lower 40 bits denote a peculiar ID unique by body. Then, the peculiar ID generates an effect that identification of the body becomes easy by setting (inputting) a MAC address for Ethernet (registered trademark) which already becomes a unique value every body. This is because the MAC address is an ID number unique to each Ethernet (registered trademark) card and numbers unique to each sheet are assigned to global Ethernet (registered trademark) cards respectively. Hence, IEEE 1394 identification information can be made common use with a MAC address of Ethernet (registered trademark) by using the MAC address for an IEEE 1394 identification number.

As a setup method, as illustrated in FIG. 9, at the time of power-up, when a MAC address is transmitted to a body (for example, IEEE 1394 DV signal generating circuit 35 in FIG. 1) on IEEE 1394 from the main CPU 16, the IEEE 1394 DV signal generating circuit 35 stores the information therein, and answers the value as body identification information to an external device 39 for a response from the external device 39.

Fifth Embodiment

Figure 10:
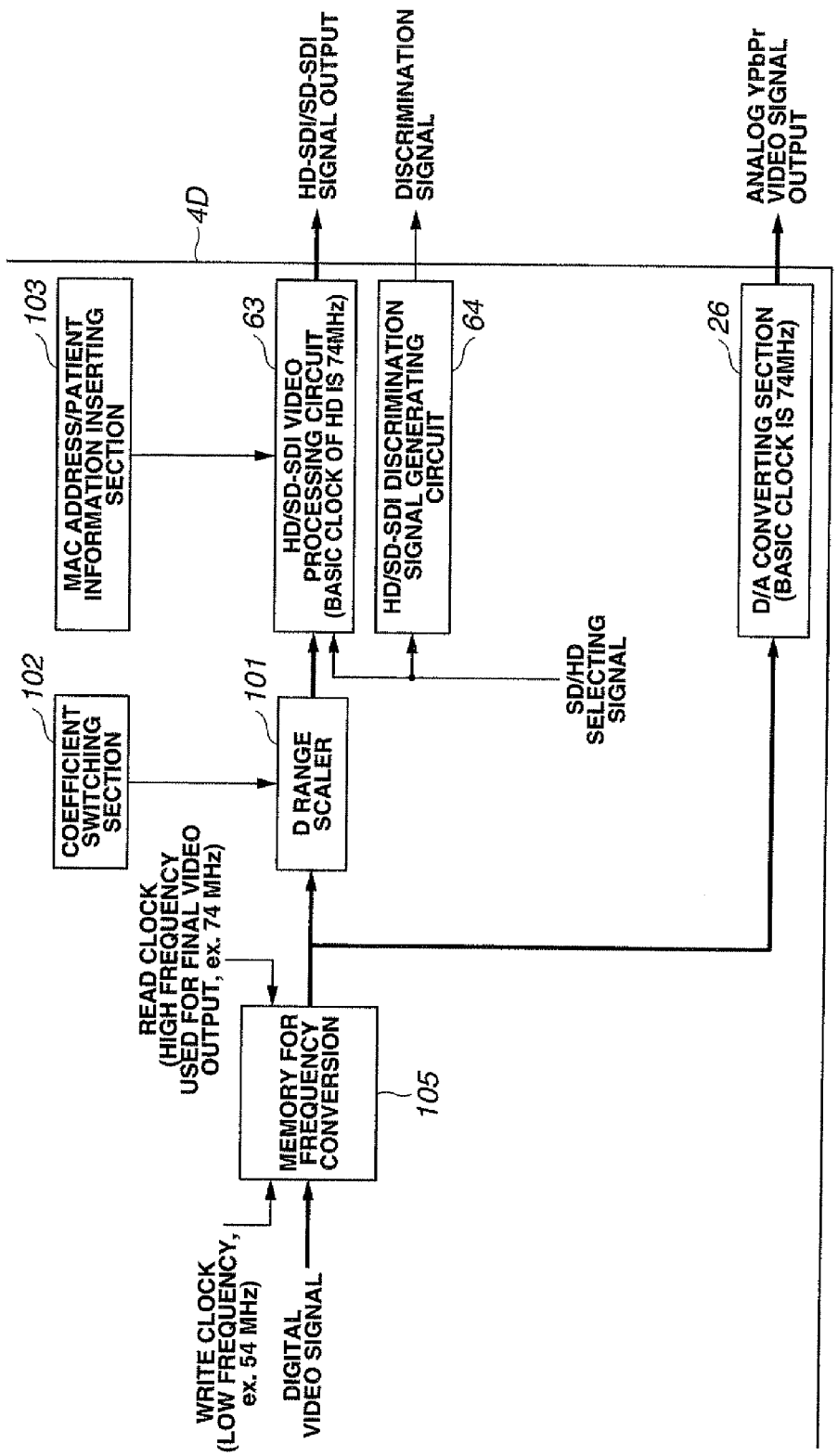
FIG. 10 is a block diagram illustrating a configuration at the time of an HDTV output in configuration of a final video output portion of a video processor in an endoscope apparatus of a fifth embodiment of the present invention.

FIG. 10 illustrates configuration of a final video output portion of a video processor in an endoscope apparatus of a fifth embodiment of the present invention. FIG. 10 illustrates the configuration of omitting the IEEE 1394 DV signal generating circuit 35 similarly to FIG. 6.

Medical equipment needs not making equipment used concurrently also including a treatment tool for an operation malfunction from an aspect of risk aversion, and it is desirable to make it operate at a low clock rate.

Then, in the fifth embodiment, by setting a frequency of a clock used for video processing and transmission between boards in an endoscope apparatus lower than a clock used for a final video output, it is made that a video signal at a low clock is transmitted between boards to suppress electromagnetic radiation noise by EMC (Electro-Magnetic Compatibility). In addition, since, for example, a video processor has large circuit scale and is configured of two or more sheets of wiring boards, transmission between boards means to perform signal transmission between the boards with distribution cables.

In FIG. 10, different points from FIG. 6 are (1) to set a frequency of a clock of a digital video signal from the digital signal processing circuit 62 (refer to FIG. 2), which is not illustrated, lower than that of a clock which is used for a final video output, and (2) to have such configuration of providing memory 105 for frequency conversion which writes a digital video signal from the above-mentioned digital signal processing circuit 62 at a low clock rate (54 MHz) and reads it at a high clock rate (74 MHz), and supplying it to the D range scaler 101 through this. Other circuitry is the same as that of FIG. 5. As described in FIG. 5, the basic clock in the HD/SD-SDI video processing circuit 63 and the D/A converting section 26 is 74 MHz which is a comparatively high clock frequency. This is because an HDTV basic clock (driving clock) of the monitor 5 connected to a post-stage of a video processor 4D is generally specified at 74 MHz.

An implementation method will be described below.

A minimum clock frequency at the time of processing a video signal is found from (horizontal effective pixel count+ pixel count of a blanking necessary for update of data)× (effective line count+line count of a blanking necessary for update of data)×frame rate (30/1.001).

Next, in consideration of ease of performing the video processing of a whole system, a clock used for video signal processing is set to a frequency between the minimum clock frequency which is found and a frequency used in the final video output.

A frequency of a synchronizing signal necessary for video signal processing is also adjusted to the above-mentioned video signal whose clock rate is made low to be made into (horizontal effective pixel+pixel count of blanking necessary for data update) horizontally, and to be made into a vertical direction sets as (effective vertical line number+line count of blanking necessary for data update).

Then, as mentioned above, before the final video output, the memory 105 performs frequency conversion of 54 MHz/ 74 MHz to perform rate conversion from a low-rate clock (54 MHz) to a clock (74 MHz) on the normal video standard and output it. Thereby, since it is possible to lower a transmission frequency in transmission between boards and to decrease electromagnetic radiation noise, it is effective as a measure against EMC.

In addition, although the frequency of the clock used for Hi-Vision (HDTV) is made 74 MHz, since this is vertical: 1125 lines, horizontal: 2200 pixels, and 29.94I, it is found from 1125×2200×(30/1.001)=74.1758 MHz.

Figure 11:
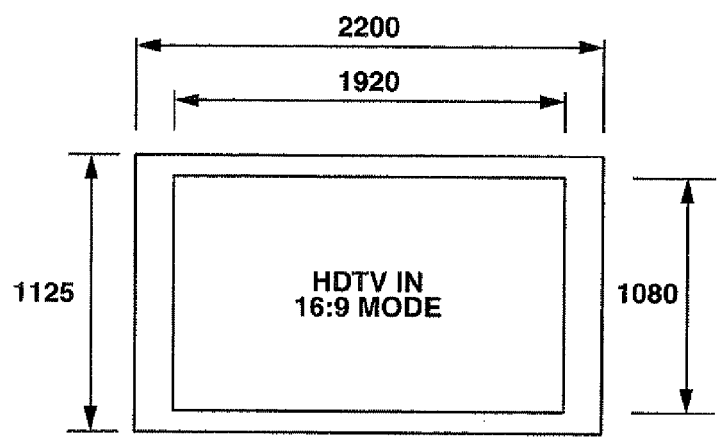
FIG. 11 is a drawing illustrating a format and a 16:9 display mode about an HDTV signal.
Figure 12:
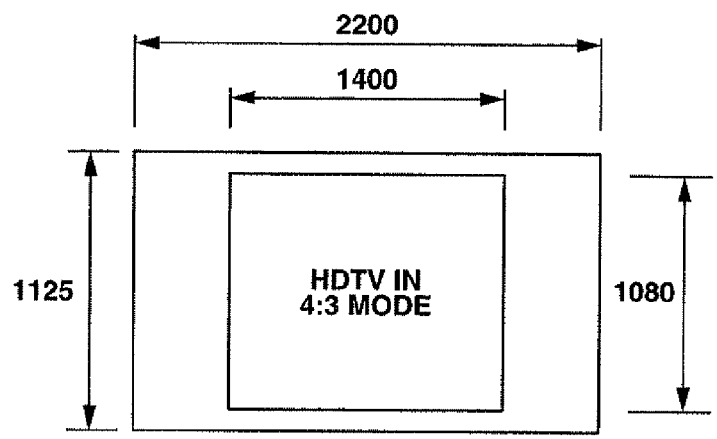
FIG. 12 is a drawing illustrating a format and a 4:3 display mode about an HDTV signal.

FIGS. 11 and 12 illustrate formats and two kinds of display modes about the HDTV signal. The pixel count of a vertical× horizontal format of the HDTV is 1125×2200. In FIG. 11, a pixel count of an effective video of the HDTV in a 16:9 mode is 1080×1920, and 74 MHz is used for video signal processing. In addition, in FIG. 12, a pixel count of an effective video in a 4:3 mode in the HDTV is 1080×1440, and since effective pixels are few, video signal processing at 54 MHz is sufficient.

Hence, when the monitor 5 is used in the display mode in FIG. 11, since it is possible to set the frequency of the clock used for transmission between boards low by the configuration of arranging the memory 105 for frequency conversion which is illustrated in FIG. 10, it is possible to reduce EMC noise. When the monitor 5 is used in the display mode in FIG. 12, since the memory 105 for frequency conversion illustrated in FIG. 10 becomes unnecessary, a monitor output can be performed also with the clock rate of a low frequency, it becomes sufficient not to take a measure against EMC noise particularly.

INDUSTRIAL APPLICABILITY

The present invention is applicable to an endoscope apparatus which generates various kinds of serial digital video signals from an image pickup signal by a solid state image pickup element mounted in an endoscope, and is connected to an external device through a connector for external connection.

The present application is applied with setting Japanese Patent Application No. 2005-166203 filed on Jun. 6, 2005 in Japan as a base of a claim of priority, and the above-mentioned content of disclosure shall be cited in Scope of Claim of the present application specification.

The invention claimed is:

1. An image processing apparatus for an endoscope, comprising:
 a video signal generating section configured to process an image pickup picture signal from an endoscope, capable of generating two or more kinds of serial digital video signals having resolutions are different from one another;
 a first connector configured to output a serial digital video signal selected on the basis of a selection instruction for selecting one of the two or more kinds of serial digital video signals generated;
 a discrimination signal generating section configured to generate a discrimination signal for discriminating the serial digital video signal, selected on the basis of the selection instruction, substantially at a timing in which selection switching of the two or more kinds of serial digital video signals occurs, the discrimination signal being in a form readable in a storage device;
 a second connector configured to output the discrimination signal, wherein the second connector is different from the first connector;
 and a storing device, which is an external storage device, connected to the first and second connectors, the storing device comprising a signal processing section configured to perform signal processing corresponding to a serial digital video signal supplied through the first connector using the discrimination signal output from the second connector, and store a signal, processed by the signal processing section, on a storing medium, and the storing device uses the discrimination signal corresponding to the selection switching based on the selection instruction of the serial digital video signal, the discrimination signal being in the form readable in the storing device, to execute the signal processing of the signal processing section,
 wherein the serial digital video signal and the discrimination signal of one kind which are output according to the selection switching are supplied to the storing device.

2. The image processing apparatus for an endoscope according to claim 1, wherein the two or more kinds of serial digital video signals whose resolutions are different from one another are an HDTV serial digital video signal and an SDTV serial digital video signal.

* * * * *

UNITED STATES PATENT AND TRADEMARK OFFICE
CERTIFICATE OF CORRECTION

| | | |
|---|---|---|
| PATENT NO. | : 8,587,644 B2 | Page 1 of 1 |
| APPLICATION NO. | : 11/916721 | |
| DATED | : November 19, 2013 | |
| INVENTOR(S) | : Tsutomu Hirai et al. | |

It is certified that error appears in the above-identified patent and that said Letters Patent is hereby corrected as shown below:

On the Title Page,

It Should Read:

Item (86)  PCT No.:   PCT/JP2006/311110

§371 (C)(1),
(2), (4) Date:   Feb. 6, 2008

Signed and Sealed this
Eighth Day of April, 2014

Michelle K. Lee
*Deputy Director of the United States Patent and Trademark Office*